US009593120B2

(12) United States Patent
Rutman et al.

(10) Patent No.: US 9,593,120 B2
(45) Date of Patent: Mar. 14, 2017

(54) PARALYTIC SHELLFISH POISON

(71) Applicant: ALGENIS SPA, Huechuraba, Santiago (CL)

(72) Inventors: Max Rutman, Ñuñoa (CL);
Jean-Jacques Pilorget, Ñuñoa (CL);
Jimmy Stehberg, Providencia (CL);
Wolfgang Vanscheidt, Freiburg (DE);
Constanza Sigala, Ñuñoa (CL)

(73) Assignee: ALGENIS SPA, Santiago (CL)

( * ) Notice: Subject to any disclaimer, the term of this patent is extended or adjusted under 35 U.S.C. 154(b) by 0 days.

(21) Appl. No.: 14/385,329

(22) PCT Filed: Mar. 15, 2013

(86) PCT No.: PCT/EP2013/055448
§ 371 (c)(1),
(2) Date: Sep. 15, 2014

(87) PCT Pub. No.: WO2013/135884
PCT Pub. Date: Sep. 19, 2013

(65) Prior Publication Data
US 2015/0065528 A1   Mar. 5, 2015

Related U.S. Application Data

(60) Provisional application No. 61/613,601, filed on Mar. 21, 2012.

(30) Foreign Application Priority Data

Mar. 16, 2012   (EP) .................................... 12159932

(51) Int. Cl.
| | | |
|---|---|---|
| *A01N 43/54* | (2006.01) |
| *A61K 31/505* | (2006.01) |
| *C07D 237/36* | (2006.01) |
| *C07D 473/32* | (2006.01) |
| *A61K 31/519* | (2006.01) |
| *A61K 31/4741* | (2006.01) |
| *A61K 31/4748* | (2006.01) |
| *A61K 9/00* | (2006.01) |
| *A61K 47/12* | (2006.01) |
| *A61K 47/14* | (2006.01) |
| *A61K 47/18* | (2006.01) |
| *A61K 9/06* | (2006.01) |
| *A61K 47/32* | (2006.01) |
| *A61K 47/44* | (2006.01) |
| *A61K 31/52* | (2006.01) |
| *A61K 45/06* | (2006.01) |

(52) U.S. Cl.
CPC .......... *C07D 473/32* (2013.01); *A61K 9/0009* (2013.01); *A61K 9/0014* (2013.01); *A61K 9/06* (2013.01); *A61K 31/4741* (2013.01); *A61K 31/4748* (2013.01); *A61K 31/519* (2013.01); *A61K 31/52* (2013.01); *A61K 45/06* (2013.01); *A61K 47/12* (2013.01); *A61K 47/14* (2013.01); *A61K 47/186* (2013.01); *A61K 47/32* (2013.01); *A61K 47/44* (2013.01)

(58) Field of Classification Search
USPC .......................................... 514/267; 544/234
See application file for complete search history.

(56) References Cited

U.S. PATENT DOCUMENTS

| | | | | |
|---|---|---|---|---|
| 7,888,345 | B2 * | 2/2011 | Hoyt et al. ............... | 514/212.07 |
| 2006/0194759 | A1 * | 8/2006 | Eidelson ........................ | 514/54 |
| 2011/0086899 | A1 | 4/2011 | Winters et al. | |

FOREIGN PATENT DOCUMENTS

| | | | |
|---|---|---|---|
| CN | 1680382 A | | 10/2005 |
| WO | WO 2010/111777 | * | 10/2010 |
| WO | WO 2010/111777 A1 | | 10/2010 |
| WO | WO 2011/098539 | * | 8/2011 |
| WO | WO 2011/098539 A1 | | 8/2011 |

OTHER PUBLICATIONS

Villamil et. al. (The American Journal of Medicine (2005) 118:1160-1163).*
Greaves, Malcolm W., "Pathogenesis and Treatment of Prurituts", Current Allergy and Asthma Reports 2010, Current Medicine Group LLC GBR, ISSN: 1529-7322, XP002694800, vol. 10, No. 4, Jul. 2010, pp. 236-242.
International Search Report issued in PCT/EP2013/055448, mailed on May 14, 2013.
Roberson et al., Abstract of "TRPV1 mediated delivery of the impermeant sodium-channel blocked QX-314 into pruriceptors blocks itch", Society for Neuroscience, Abstract Viewer and Itinerary Planner, 39th Annual Meeting of the Society-for-Neuroscience, Chicago, IL, USA, XP009165188, Oct. 17-21, 2009.
Villamil et al., "Efficacy of lidocaine in the treatment of pruritus in patients with chronic cholestatic liver diseases", The American Journal of Medicine, Excerpta Media, Inc., United States, XP027728743, vol. 118, No. 10, Oct. 1, 2005, pp. 1160-1163.
Written Opinion issued in PCT/EP2013/055448, mailed on May 14, 2013.

* cited by examiner

*Primary Examiner* — Marcos Sznaidman
(74) *Attorney, Agent, or Firm* — Birch, Stewart, Kolasch & Birch, LLP

(57) ABSTRACT

The invention concerns a paralytic shellfish poison for the treatment of itching in a human being or another mammal.

28 Claims, 1 Drawing Sheet

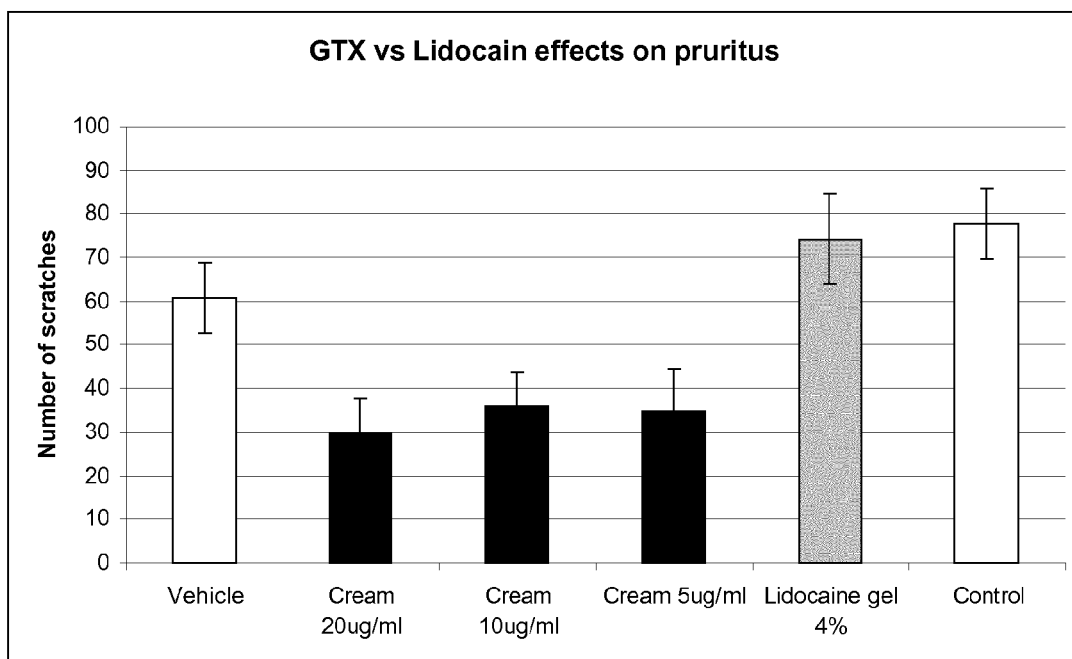

PARALYTIC SHELLFISH POISON

CROSS REFERENCE TO RELATED APPLICATIONS

This application is the National Phase of PCT International Application No. PCT/EP2013/055448, filed on Mar. 15, 2013, which claims priority under 35 U.S.C. 119(e) to U.S. Provisional Application No. 61/613,601, filed on Mar. 21, 2012, and under 35 U.S.C. 119(a) to patent application Ser. No. 12/159,932.8, filed in Europe on Mar. 16, 2012, all of which are hereby expressly incorporated by reference into the present application.

The invention concerns paralytic shellfish poison for the treatment of a human being or another mammal and a pharmaceutical composition comprising that paralytic shellfish poison as well as method of treatment.

Itch is a principal symptom of skin disease and is an important skin manifestation of systemic disease. Microneurography technique has established the existence of dedicated slow-conducting unmyelinated C neurons which only transmit itch (and temperature changes) in response to histamine—thus disproving the notion that itch is merely a mild version of pain. These neurons, which represent only about 5% of the total, have also been shown to be selectively activated in chronic pruritic skin disease. Microneurography has also established that the contralateral transmission neurones which convey itch to the thalamus consist of an itch specific subclass of lamina 1 spinothalamic tract neurons, thus establishing that dedicated neurons transmit itch not only peripherally but also centrally.

Pruritus can be classified pathophysiologically into 4 categories:
- pruritoceptive—generated in the skin usually by an inflammatory or other visible pathological process, e.g., scabies, urticaria,
- neurogenic—generated in the central nervous system in response to circulating pruritogens as in cholestasis or in response to intraspinal morphine,
- neuropathic—due to anatomical lesions of the central or peripheral nervous systems, e.g., nerve entrapment, tumours and
- psychogenic, including delusional parasitosis.

For the treatment of pruritus antihistamines are usually poorly effective unless the pruritus is principally mediated by histamine, e.g., urticaria, although the sedative action of the first-generation H1 antihistamines may be useful in other cases of chronic pruritus.

Corticosteroids are not intrinsically antipruritic and are only effective in relieving pruritus occurring as a consequence of inflammatory changes in the skin.

Narrow band ultraviolet B phototherapy (311 nanometers) is beneficial in generalised itching due to most causes, and is especially useful in pruritus of end-stage renal failure.

Doxepin, a tricyclic compound, is a non-specific inhibitor of post-synaptic re-uptake of adrenaline and noradrenaline and is a powerful antipruritic, possessing greater potency as an H1 antihistamine than any other available H1 antagonist as well as being widely used as an antidepressant. It should be prescribed in low dosage initially, and be used with extreme caution in patients with liver or cardiovascular disease. It should not be withdrawn abruptly or prescribed concurrently with other antidepressants. It is not contraindicated in the presence of renal failure and is thus very useful in these patients. It is metabolised via the liver cytochrome P450 3A pathway and therefore should not be administered concurrently with macrolide antibiotics or imidazole antifungals.

Opioid antagonists, including oral naltrexone, are effective in some patients, especially in patients with cholestatic itching. This class of drug is contraindicated in patients with severe liver disease, patients addicted to opioids and patients receiving opioid analgesia. Opioid antagonists seem to cause withdrawal symptoms and signs in patients with itching due to cholestasis and dosage should start low and be increased gradually to avoid this complication.

Butorphanol, a combined μ-receptor antagonist and κ-receptor agonist, administered as a nasal spray, has showed considerable promise in the management of intractable pruritus. Gabapentin, a structural analogue of γ-amino butyric acid and an anticonvulsant, has been advocated as a potent antipruritic and has received support from at least 1 double blind placebo-controlled trial in haemodialysis patients. Other drugs that can be tried include mirtazepine, a serotonin type 3 receptor antagonist, paroxetine, a selective serotonin reuptake inhibitor (SSRI) and thalidomide.

The sodium channel blocker lidocaine and other local anaesthetics have been reported to cause side effects including itching and/or local hypersensitivity reactions. Other Na channel blockers such as local Novocain has also been reported to cause allergic reactions including itching.

From Villamil, A. G. et al., The American Journal of Medicine (2005) 118, pages 1160-1163 it is known to use lidocaine in the treatment of pruritus in patients with chronic cholestatic liver diseases. For the treatment the lidocaine is administered intravenously.

From US 2011/0086899 A1 it is known to use a spiro-oxindole compound for the treatment of pruritus by oral administration.

From Roberson, D. P. et al., Society for Neuroscience, Abstract Viewer and Itinerary Planner, vol. 39, 2009, $39^{th}$ Annual Meeting of the Society for Neuroscience, Chicago, Ill., USA, Oct. 17 to 21, 2009 discloses that TRPV1 mediated delivery of the impermeant sodium channel blocker QX-314 into pruriceptors blocks itch. However, this requires a co-application of a TRPV1 agonist together with QX-314.

From WO 2011/098539 A1 the use of the sodium channel blocker saxitoxin and its derivatives for a method of treatment of a reduction or loss of superficial sensitivity or sense of touch is known. This application discloses that superficial sensitivity is so much enhanced by the treatment that the reduced or lost superficial sensitivity or sense of touch is at least partly restored.

From WO 2010/111777 A1 it is known to use tetrodotoxin galactopyranosides for the treatment of itching.

CN 1680382 A discloses the use of tetrodotoxin as antipruritic agent.

The problem to be solved by the present invention is to provide a further substance and a further pharmaceutical composition as well as a further method for the treatment of itching without a loss of sensitivity in an area innervated by nerves affected by the treatment in a human being or another mammal.

The problem is solved by the subject-matter of claims 1, 11 and 18. Embodiments of the invention are subject matter of claims 2 to 10, 12 to 17 and 19 to 21.

According to the invention a paralytic shellfish poison (PSP) for use in a method of treatment of itching in a human being or another mammal is provided. The PSP is saxitoxin or a tricyclic 3,4-propinoperhydropurine represented by the following formula (I)

Formula I wherein $R_1$ and $R_5$ are independently selected from the group consisting of —H and —OH; $R_2$ and $R_3$ are independently selected from the group consisting of —H, —OSO$_3^-$ and —SO$_3$; and $R_4$ is selected from the group consisting of —H, —OH, —OC(=O)NH$_2$, —OC(=O)NHSO$_3^-$ and —OC(=O)CH$_3$. The PSP may also be a salt of saxitoxin or the tricyclic 3,4-propinoperhydropurine.

The paralytic shellfish poison may be administered once, over a period of one to seven days, in multiple treatment cycles and/or in chronic treatment.

The inventors of the present invention have recognized that the PSP according to the invention has an anti-itching effect that differs from the effect of other sodium channel blockers such as lidocaine. Up to now none of the side effects of lidocaine and other non-PSP local anesthetics has been found for PSP. If itching is treated with lidocaine, sensitivity is lost in the area innervated by nerves affected by the treatment. This is not the case if itching is treated with PSP according to the invention in a concentration and an amount that is only sufficient for a reduction or elimination of itching but not sufficient to cause a loss in sensitivity. Such concentration and amount can easily be determined by testing different concentrations and amounts, e.g. by application to skin. The anti-itching effect of the PSP according to the invention is a complete new effect.

WO 2011/098539 A1 discloses the same sodium channel blockers as have been recognized by the inventors to be useful for the treatment of itching. However, the sodium channel blockers disclosed in WO 2011/098539 A1 enhance sensitivity of the skin such that a reduced or lost superficial sensitivity or sense of touch is at least partly restored. Enhancing sensitivity would be expected to enhance itching. Therefore, it is very astonishing that these sensitivity enhancing substances can be used to reduce itching.

In an embodiment of the invention either one of $R_2$ and $R_3$ is —OSO$_3^-$ or $R_4$ is —OC(=O)NHSO$_3^-$. The tricyclic 3,4-propinoperhydropurine may be one of the derivatives of saxitoxin or a gonyautoxin (hereinafter "GTX") according to formula I as set forth in the table below.

In one embodiment the PSP according to the invention is in the form of its racemate, pure stereoisomer, especially enantiomer or diastereomer or in the form of a mixture of stereoisomers, especially enantiomers or diastereomers, in neutral form, in the form of an acid or base or in the form of a salt, especially a physiologically acceptable salt, or in the form of a solvate, especially a hydrate.

In one embodiment the PSP according to the invention is saxitoxin, neosaxitoxin, descarbamoylsaxitoxin, or GTX, in particular GTX-1, GTX-2, GTX-3, GTX-4, or GTX-5, wherein the saxitoxin, neosaxitoxin, descarbamoylsaxitoxin, or GTX, in particular GTX-1, GTX-2, GTX-3, GTX-4, or GTX-5, is synthetically synthesized or isolated from a biological source, in particular from cyanobacteria, from dinoflagellates or from contaminated shellfish, especially shellfish contaminated with *A. catenella*.

The saxitoxin, neosaxitoxin, descarbamoylsaxitoxin, or GTX, in particular GTX-1, GTX-2, GTX-3, GTX-4, or GTX-5, may be used in an amount of 0.01 µg/day to 1000 µg/day, in particular 0.1 to 100 µg/day, especially 1 to 10 µg/day.

The PSP according to the invention may also be the tricyclic 3,4-propinoperhydropurine, wherein the tricyclic 3,4-propinoperhydropurine is synthetically synthesized or isolated from a biological source.

The itching to be treated may be of pruritoceptive nature, of neurogenic nature, of neuropathic nature, of psychogenic nature, due to an inflammatory process, due to an insect bite, due to an inflammatory process, in particular an inflammatory process due to surgery or healing, due to infectious process, in particular an infectious process caused by a virus, bacteria, a fungus or prions, due to circulating pruritogens, due to a systemic pathology, in particular cholithiasis or acute or chronic renal insufficiency, due to any allergen exposure, due to tobacco exposure, in particular smokeless tobacco exposure, due to chemical exposure, or due to respiratory cause. The inflammatory process may be any inflammatory process regardless of the intrinsic cause of the process.

The PSP according to the invention may be for use by oral administration, by injection, in particular intramuscular, intravenous, intradermal or subcutaneous injection, by topical administration, in particular by use of a skin-patch, a cream, an ointment or a spray and/or by use of a physical transdermal delivery method, in particular by iontophoresis, phonophoresis, sono-macroporation, thermal modulation or magnetic modulation or by use of a physical device, in particular a respiratory device, in particular a nebulizer.

The invention further concerns a pharmaceutical composition comprising at least one paralytic shellfish poison according to the invention and a pharmacologically acceptable carrier for use in a method of treatment of itching in a human being or another mammal. The carrier may be any material suitable for topical, in particular superficial, drug administration. Carriers include any such materials known

| Compound | $R_1$ | $R_2$ | $R_3$ | $R_4$ | $R_5$ |
| --- | --- | --- | --- | --- | --- |
| Gonyautoxin 1 | —OH | —H | —OSO$_3^-$ | —OC(=O)NH$_2$ | —OH |
| Gonyautoxin 2 | —H | —H | —OSO$_3^-$ | —OC(=O)NH$_2$ | —OH |
| Gonyautoxin 3 | —H | —OSO$_3^-$ | —H | —OC(=O)NH$_2$ | —OH |
| Gonyautoxin 4 | —OH | —OSO$_3^-$ | —H | —OC(=O)NH$_2$ | —OH |
| Gonyautoxin 5 | —H | —H | —H | —OC(=O)NHSO$_3^-$ | —OH |
| Neosaxitoxin | —OH | —H | —H | —OC(=O)NH$_2$ | —OH |
| Descarbamoylsaxitoxin | —OH | —H | —H | —OH | —OH | in the art which is non-toxic in the amount used, and does not interact with other components of the composition in deleterious manner.

In an embodiment the PSP according to the invention is contained in the pharmaceutical composition in an amount suitable for an administration of 0.01 to 1000 µg, in particular 0.1 to 100 µg, especially 1 to 10 µg, PSP per day. The PSP according to the invention may be contained in the pharmaceutical composition in a concentration of 0.01 to 1000 µg per ml, in particular 0.1 to 100 µg per ml, especially 1 to 10 µg per ml.

The pharmaceutical composition according to the invention may be a pharmaceutical composition prepared for injection, in particular intramuscular, intravenous, intradermal, or subcutaneous injection, prepared for topical administration, in particular superficial administration, or prepared for systemic administration, in particular oral administration.

The pharmaceutical composition prepared for superficial administration can be a skin-patch, a cream, an ointment, or a spray.

According to an embodiment of the invention the pharmaceutical composition further comprises at least one antipruritic compound. The antipruritic compound may be, without being limited thereto, an antihistaminic compound such as chlorphenamine, loratadine or desloratadin, a corticosteroid such as betamethasone, clobetasol or mometasone, or a non-steroidal anti-inflammatory drug such as ibuprofen, ketoprofen or diclofenac.

The PSP in the pharmaceutical composition according to the invention may be contained in a liposome or a microemulsion. A microemulsion is a stable, isotropic liquid mixture of oil, water and surfactant, frequently in combination with a cosurfactant. The mixture is an emulsion with oil dispersed in water or water dispersed in oil the dispersed phase of which is forming such small domains that visible light is not scattered by the dispersed phase. Therefore, the microemulsion is clear.

Alternatively or in addition the pharmaceutical composition comprising the PSP may further comprise at least one substance facilitating the transport of the PSP through the skin. Such substances are known in the art as permeation enhancers. The substance may be a substance selected from the group consisting of: alcohols, amines, amides, amino acids, amino acid esters, 1-substituted azacycloheptan-2-ones, pyrrolidones, terpenes, fatty acids, fatty acid esters, macrocyclic compounds, tensides, sulfoxides, liposomes, transferomes, lecithin vesicles, ethosomes, anionic, cationic and non-ionic surfactants, polyols, essential oils, dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, a poloxamer, polysorbate 20 (Tween 20=polyoxyethylene sorbitan monolaurate), polysorbate 40 (Tween 40=polyoxyethylene sorbitan monopalmitate), polysorbate 60 (Tween 60=polyoxyethylene sorbitan monostearate), polysorbate 80 (Tween 80=polyoxyethylene sorbitan monooleate), lecithin, 1-n-dodecylcyclazacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, polyethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

The poloxamer (polyethylene-polypropylene glycol, molecular formula $HO(C_2H_4O)_a(C_3H_6O)_b(C_2H_4O)_aH$, wherein a and b are integers) is a synthetic nonionic triblock block copolymer composed of a central hydrophobic chain of polyoxypropylene (poly(propylene oxide)) flanked by two hydrophilic chains of polyoxyethylene (poly(ethylene oxide)). It is available in several types such as Poloxamer 231, Poloxamer 182, or Poloxamer 184.

The invention further concerns a method of treatment of itching in a human being or another mammal, wherein the PSP or the pharmaceutical composition according to the invention is administered to the human being or other mammal. The PSP or the pharmaceutical composition may be administered by way of injection, in particular intramuscular, intravenous, intradermal, or subcutaneous injection, by way of topical administration, in particular superficial administration, or by way of systemic administration, in particular oral administration. Administration may be supported physically, in particular by iontophoresis, phonophoresis, sonomacroporation, thermal modulation or magnetic modulation. The PSP or the pharmaceutical composition may be administered over a period of one to seven days and/or in multiple treatment cycles

EMBODIMENTS

To design a study where the effects of the PSP toxin on itching can be assessed, the two most commonly used itching models in rats were compared; subcutaneous injections of serotonin or histamine. Such injections have been reported to induce increased scratching in the injected zone.

The following preparations were used for animal tests:
a) Serotonin-Solution: Serotonin hydrochloride 2.5 mg/Kg (Enzo Life Sciences) dissolved in saline (0.9% NaCl).
b) Gel test formulation v1 234: GTX 2/3 (Cetiol SB-45, Panalene L-14-E, Ceteary Alc-Ceteareth 20, Glucamate SS, Glucamate SSE 20, Propylparaben, Methylparaben, Carbopol 2020, Glycerine, water, Trietanolamine, Silicone DC 345, Microcare PM5, Sepigel 305.
c) 110214 PB GTX: GTX 2/3 in Saline (0.9% NaCl).
d) Three GTX toxin preparations: GTX 2/3+liposome (water, *Persea Gratissima* Oil, Propylene Glycol, Squalane, Petrolatum, Dimethicone, PEG-20 Methyl Glucose Sesquistearate, Cetyl Acetate (y) Acetylated Lanolin Alcohol, Diazolinidyl Urea (y) Methylparaben (y), Propylparaben (y) Propylene Glycol, Glyceryl Stearate, Methyl Glucose, Sesquistearate, Triethanolamine, Ozokerite, Carbomer Acrylates/C 10-30 Alkyl Acrylate Crosspolymer, Tocopherol (y) ascorbyl Palmitate (y) Lecithin, (y) Glyceryl Stearate (y) Glyceryl Oleate (y) Citric Acid). Composition as described before with GTX 2/3 5, 10 and 20 µg/g of cream.
e) Vehicle: As "d", but without GTX 2/3 (Placebo).
f) Lidocaine gel 4%: Lidocaine Hydrochloride LCH Gel 4%+excipients 1. Effects of the Toxin in Subcutaneous Serotonin-Induced Itching Rationale: The objective was to test the effects of the toxin in subcutaneous serotonin (5-HT)-induced itching, which is the most commonly used and effective method to attain itching in rats. As the toxin cream preparation shows only cutaneous effects, we decided to test the effects of the cream preparation on the skin and subcutaneous co injection of serotonin with the toxin.

Methods: After acclimation and trimming male rats were divided into 3 groups. The first group was injected subcutaneously with serotonin (50 μl of 5HT (2.5 mg/kg). The second group had the gel test formulation v1 234 applied (between 80-100 mg) to the trimmed region 1 hour before subcutaneous injection of serotonin (same dose as above). The third group was co injected with a mixture of the toxin (10 μg/kg 110214 PB GTX) and serotonin (2.5 mg/kg in 50 μl). Animal behaviour was measured for 30 minutes since the subcutaneous injections.

Results: Subcutaneous injection of serotonin in the neck induced an increase in scratches (5HT) which was mildly ameliorated by co injection of the toxin and serotonin (5HT-toxin). The application of the toxin gel induced a non significant increase in scratches.

Conclusions: The data suggest that the toxin co injected subcutaneously with serotonin has an effect in itching.

2. Effects of the Toxin in Cutaneous Serotonin-Induced Itching

Rationale: The objective was to test the effects of the toxin in cutaneous serotonin (5-HT)-induced itching.

Methods: After acclimation and trimming (see above) male rats had the gel test formulation v1 234 applied (between 80-100 mg) to the trimmed region 1 hour before cutaneous application of serotonin (same dose as above).

Results: A significant reduction of the scratching behaviour in the animals is observed after cutaneous toxin application.

Conclusions: GTX in gel induces an over 60% reduction of itching in cutaneous serotonin-induced itching in rats.

3. Comparison with Lidocaine

Methods: Male Sprague Dawley rats weighing between 250-300 grams were handled once a day for 5 days. On the test day rats were trimmed on a 2×2 cm region of their right side of the neck. Animals were divided into 6 groups (N=8 each). The first 4 groups were treated cutaneously by rubbing 80-100 mg on the bare skin either with GTX toxin preparations or the vehicle one hour before serotonin application. One group of rats was treated cutaneously with lidocaine gel 4% (80-100 mg) 5 minutes before serotonin application. The last group did not receive any cutaneous treatment. Serotonin (100 μl, 2.5 mg/kg) was applied cutaneously to all animals. Rats were then placed in their individual homecages, and animal behaviour was recorded as the number of scratches within 30 minutes from serotonin application. Two consecutive scratches were considered different if a 1 second interval was present between them.

Results: As can be seen in the figure, the three concentrations of GTX (5, 10 and 20 μg/g of cream) produced significant decreases in serotonin-induced scratching behaviour (over 50% decrease for 20 μg/g cream; $p<0.01$). Neither the vehicle nor lidocaine gel had significant effects on serotonin-induced pruritus.

4. Therapeutic Applications

The following cream composition was used for all therapeutic applications described below:

| Ingredient | Concentration |
| --- | --- |
| Aqua | 70.400 |
| *Persea Gratissima* Oil | 6.000 |
| Propylene Glycol | 5.000 |
| Squalane | 3.500 |
| Mixture of the epimers GTX-2 and GTX-3 | 1.000 |
| Petrolatum | 3.500 |
| Dimethicone | 3.000 |
| PEG-20 Methyl Glucose Sesquistearate | 2.500 |
| Cetyl Acetate and Acetylated Lanolin Alcohol | 2.000 (total concentration of the mentioned ingredients) |
| Diazolinidyl Urea and Methylparaben and Propylparaben and Propylene Glycol | 1.500 (total concentration of the mentioned ingredients) |
| Glyceryl Stearate | 1.000 |
| Methyl Glucose Sesquistearate | 0.500 |
| Triethanolamine | 0.300 |
| Ozokerite | 0.300 |
| Carbomer | 0.050 |
| Acrylate(s) | 0.200 |
| Perfume | 0.150 |
| Tocopherol and Ascorbyl Palmitate and Lecithin and Glyceryl Stearate and Glyceryl Oleate and Citric Acid | 0.100 |

The acrylate(s) may be C 10-30 alkyl acrylate crosspolymer(s).

A sixty year old man presented with a mosquito bite in his neck. He locally applied the cream composition with a relief of the itching within 10 to 15 minutes. He referred that he did not need further application.

A seventy year old man presented with a skin allergic reaction on both his legs with intense itching and mild to moderate swelling. He locally applied the cream composition with relief of the symptoms within about half an hour. He referred that he has applied the GTX preparation two to three times during 24 hours to obtain a complete relief of the symptoms.

A 79 years old woman with severe itching due to prurigo Hyde had immediate relief from itching from VAS-analogue scale 8 to 2 by application of the cream composition.

Severely itching of a 57 years old man with dyshidrotic hand eczema had been classified VAS-analogue scale 5. After one application of the cream composition the itching was down to zero. The effect lasted almost exactly for 24 h.

A 40 year old woman had an extremely itching angry brown patch on the back. After the first application the itching was gone. This effect lasted under once daily application for 24 h. The itching recurred after the cream was no longer applied.

The invention claimed is:

1. A method for treatment of itching in a human being, said method comprising:
topically administering to the human being a therapeutically effective amount of a paralytic shellfish poison (PSP), wherein the PSP is saxitoxin or a salt thereof, or a tricyclic 3,4-propinoperhydropurine represented by the following formula (I) or a salt thereof, Formula I wherein
$R_1$ and $R_5$ are independently selected from the group consisting of —H and —OH;

$R_2$ and $R_3$ are independently selected from the group consisting of —H, —OSO$_3^-$ and —SO$_3$; and $R_4$ is selected from the group consisting of —H, —OH, —OC(=O)NH$_2$, —OC(=O)NHSO$_3^-$ and —OC(=O)CH$_3$.

2. The method according to claim 1, wherein the administering is supported physically.

3. The method according to claim 1, wherein the PSP is administered over a period of one to seven days and/or in multiple treatment cycles.

4. A method for treatment of itching in a human being, said method comprising:
topically administering to the human being a therapeutically effective amount to treat itching of a pharmaceutical composition, comprising at least one paralytic shellfish poison (PSP); and a pharmacologically acceptable carrier,
wherein the PSP is saxitoxin or a salt thereof, or a tricyclic 3,4-propinoperhydropurine represented by the following formula (I) or a salt thereof, Formula I wherein
$R_1$ and $R_5$ are independently selected from the group consisting of —H and —OH;
$R_2$ and $R_3$ are independently selected from the group consisting of —H, —OSO$_3^-$ and —SO$_3$; and
$R_4$ is selected from the group consisting of —H, —OH, —OC(=O)NH$_2$, —OC(=O)NHSO$_3^-$ and —OC(=O)CH$_3$.

5. The method according to claim 1, wherein the administering is supported physically by iontophoresis, phonophoresis, sono-macroporation, thermal modulation or magnetic modulation.

6. The method according to claim 1, wherein the PSP is contained in a liposome.

7. The method according to claim 1, wherein the PSP is comprised in a pharmaceutical composition at a concentration of 1 μg to 100 μg per ml of the pharmaceutical composition.

8. The method according to claim 4, wherein the PSP is contained in a liposome.

9. The method according to claim 4, wherein the PSP is at a concentration of 1 μg to 100 μg per ml of the pharmaceutical composition.

10. The method according to claim 4, wherein the PSP is in the form of its racemate, pure stereoisomer, enantiomer or diastereomer or in the form of a mixture of stereoisomers, enantiomers or diastereomers, in neutral form, in the form of an acid or base or in the form of a salt, a physiologically acceptable salt, or in the form of a solvate, or a hydrate.

11. The method according to claim 1, wherein the PSP is synthetically synthesized or isolated from a biological source.

12. The method according to claim 1, wherein the PSP is synthetically synthesized or isolated from a biological source selected from the group consisting of cyanobacteria, dinoflagellates and contaminated shellfish.

13. The method according to claim 1, wherein the PSP is isolated from shellfish contaminated with A. catenella.

14. The method according to claim 1, wherein the PSP is used in an amount of 0.01 μg/day to 1000 μg/day.

15. The method according to claim 1, wherein the PSP is used in an amount of 0.1 to 100 μg/day.

16. The method according to claim 1, wherein the PSP is used in an amount of 1 to 10 μg/day.

17. The method according to claim 1, wherein the itching is of pruritoceptive nature, of neurogenic nature, of neuropathic nature, of psychogenic nature, due to an inflammatory process, due to an insect bite, due to an inflammatory process, an inflammatory process due to surgery or healing, due to infectious process, an infectious process caused by a virus, bacteria, a fungus or prions, due to circulating pruritogens, due to a systemic pathology, cholelithiasis or acute or chronic renal insufficiency, due to any allergen exposure, due to tobacco exposure, smokeless tobacco exposure, due to chemical exposure, or due to respiratory cause.

18. The method according to claim 1, wherein the PSP is for a single use or for use over a period of one to seven days, for use in multiple treatment cycles, and/or for use in chronic treatment.

19. The method according to claim 1, wherein administration is by topical administration by use of a skin-patch, a cream, an ointment or a spray and/or by use of a physical transdermal delivery method, iontophoresis, phonophoresis, sono-macroporation, thermal modulation or magnetic modulation or by use of a physical device, respiratory device, or a nebulizer.

20. The method according to claim 4, wherein the pharmaceutical composition is prepared for topical administration.

21. The method according to claim 4, wherein the PSP is contained in the pharmaceutical composition in an amount suitable for an administration of 0.01 to 1000 μg.

22. The method according to claim 4, wherein the PSP is contained in the pharmaceutical composition in an amount suitable for an administration of 0.01 to 100 μg.

23. The method according to claim 4, wherein the PSP is contained in the pharmaceutical composition in an amount suitable for an administration of 1 to 10 μg.

24. The method according to claim 4, wherein the pharmaceutical composition is prepared for topical administration and is a skin-patch, a cream, an ointment, or a spray.

25. The method according to claim 4, wherein the pharmaceutical composition further comprises at least one antipruritic compound, an antihistaminic compound, chlorphenamine, loratadine or desloratadin, a corticosteroid, betamethasone, clobetasol or mometasone, or a non-steroidal anti-inflammatory drug, ibuprofen, ketoprofen or diclofenac.

26. The method according to claim 4, wherein the PSP is contained in a liposome or a microemulsion and/or wherein the pharmaceutical composition further comprises at least one substance facilitating the transport of the PSP through the skin, in particular a substance selected from the group consisting of: alcohols, amines, amides, amino acids, amino acid esters, 1-substituted azacycloheptan-2-ones, pyrrolidones, terpenes, fatty acids, fatty acid esters, macrocyclic compounds, tensides, sulfoxides, liposomes, transferomes, lecithin vesicles, ethosomes, anionic, cationic and non-ionic surfactants, polyols, essential oils, dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, a poloxamer, polysorbate 20 (polyoxyethylene sorbitan monolaurate), polysorbate 40 (polyoxyethylene sorbitan monopalmitate), polysorbate 60 (polyoxyethylene sorbitan monostearate), polysorbate 80 (polyoxyethylene sorbitan monooleate), lecithin, 1-n-dodecylcyclazacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, polyethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

27. The method according to claim 1, wherein the PSP is a tricyclic 3,4-propinoperhydropurine represented by formula (I) or a salt thereof, wherein $R_1$ is —H and $R_5$ is —OH; $R_2$ is —H and $R_3$ is —$OSO_3^-$ or $R_2$ is —$OSO_3^-$ and $R_3$ is —H; and $R_4$ is —OC(=O)$NH_2$.

28. The method according to claim 4, wherein the PSP is a tricyclic 3,4-propinoperhydropurine represented by formula (I) or a salt thereof, wherein $R_1$ is —H and $R_5$ is —OH; $R_2$ is —H and $R_3$ is —$OSO_3^-$ or $R_2$ is +$OSO_3^-$ and $R_3$ is —H; and $R_4$ is —OC(=O)$NH_2$.

* * * * *